United States Patent
Davis

(10) Patent No.: US 9,974,875 B2
(45) Date of Patent: May 22, 2018

(54) KEYPAD STERILIZER

(71) Applicant: Michael Davis, Raymore, MO (US)

(72) Inventor: Michael Davis, Raymore, MO (US)

(*) Notice: Subject to any disclaimer, the term of this patent is extended or adjusted under 35 U.S.C. 154(b) by 0 days. days.

(21) Appl. No.: 15/596,689

(22) Filed: May 16, 2017

(65) Prior Publication Data

US 2017/0333582 A1 Nov. 23, 2017

Related U.S. Application Data

(60) Provisional application No. 62/338,654, filed on May 19, 2016.

(51) Int. Cl.
*A61N 5/00* (2006.01)
*A61L 2/10* (2006.01)
*A61L 2/24* (2006.01)

(52) U.S. Cl.
CPC ........ *A61L 2/10* (2013.01); *A61L 2/24* (2013.01); *A61L 2202/14* (2013.01)

(58) Field of Classification Search
CPC ..... A61L 2/00; A61L 2/08; A61L 2/10; A61L 2/24
USPC ... 250/453.11, 454.11, 455.11, 492.1, 492.3, 250/493.1
See application file for complete search history.

(56) References Cited

U.S. PATENT DOCUMENTS

| 8,110,819 | B2 | 2/2012 | Boyarsky et al. | |
|---|---|---|---|---|
| 2006/0188389 | A1* | 8/2006 | Levy | A61L 2/10 422/24 |
| 2010/0058837 | A1* | 3/2010 | Quest | G01M 3/002 73/40 |
| 2012/0298890 | A1* | 11/2012 | Adiga-Manoor | H03K 17/16 250/551 |
| 2012/0321509 | A1* | 12/2012 | Bak | A61L 2/10 422/24 |
| 2015/0090903 | A1* | 4/2015 | Cole | A61L 2/10 250/492.1 |

* cited by examiner

*Primary Examiner* — Jason McCormack
(74) *Attorney, Agent, or Firm* — Erickson Kernell IP, LLC

(57) ABSTRACT

A sterilizer for point-of-sale credit card readers and keypads. One or more UV-C LEDs are integrated into the housing of the unit and directed at the keypad or other surface. The LED lights shine on the keypad or other contact surfaces, such as a stylus. Because LEDs use low DC voltage, the electronics may be powered by the keypad device power supply. The electronic circuits may be designed so that the LEDs are automatically turned on after each transaction is complete for a predetermined amount of time to kill the vast majority of pathogens that could be transmitted from person to person. The LEDs may be arranged on both the left and right side of the keypad, and at the top edge of the keypad to illuminate all exposed surfaces of the keys.

6 Claims, 2 Drawing Sheets

KEYPAD STERILIZER

CROSS REFERENCE TO RELATED APPLICATION

This application claims the benefit of provisional application Ser. No. 62/338,654, filed May 19, 2016, entitled "KEYPAD STERILIZER."

FIELD

The present invention generally relates to a sterilizer for a keypad, and more particularly, to a sterilizer utilizing ultra-violet light to disinfect a keypad.

BACKGROUND

Over the last several years, there has been tremendous advancement in understanding how sickness and diseases are spread by pathogens. Hard surfaces that people touch can harbor pathogens for hours. There are flu viruses that can live on hard surfaces for 24 hours or more. Methicillin-resistant *Staphylococcus Aureus* (MRSA) infection is caused by a type of staph bacteria that's become resistant to many of the antibiotics used to treat ordinary staph infections. MRSA infection can live for weeks on hard surfaces.

When a person touches an infected surface and immediately touches their face, bites their nails, or scratches an open wound, those pathogens may be easily transmitted to a new person, causing them to get sick and the cycle continues. As a result, there are numerous chemical products on the market to help reduce person-to-person transmission of pathogens from casual contact with the surfaces they touch. Hand sanitizer, chemical sprays and wipes are typically used to disinfect surfaces.

Despite the popularity of chemical disinfectants, there are downsides to using chemicals for the sanitation of hard surfaces and hands. Some people have allergic reactions to chemicals. Chemicals are a consumable item that requires restocking. Some chemicals, such as bleach, are caustic to a person's skin, and have an unpleasant odor. To truly be effective on hard surfaces, the chemicals need to be used after each person touches the surface, which is not practical.

As a result, there have been several inventions developed that use UV-C light to disinfect hard surfaces. These products range from a variety of wands that plug into a wall that people use to pass over an item and enclosures in which an object is placed and then the UV-C light is turned on for disinfection. All of these UV-C devices require manual operation by the user. There are also UV devices used to sanitize entire rooms such as operating rooms. Though these items may be effective at killing pathogens, they may not be used as much as they should be because they are not automatic, or are too bulky, or are cumbersome to use after each contact with a surface. In addition, these devices typically use traditional filament type bulbs that produce a lot of heat, and cannot be cycled on and off repeatedly. They require warm up and cool down cycles. If they were used in areas where they needed to be cycled hundreds of times a day those bulbs would likely burn out very quickly.

SUMMARY

The present invention provides a sterilizer for point-of-sale credit card readers and keypads. One or more UV-C LEDs are integrated into the housing of the unit and directed at the keypad or other surface. The LEDs are designed for instant on/off cycles unlike traditional mercury based bulbs. The LED lights shine on the keypad or other contact surfaces, such as a stylus. Because LEDs use low DC voltage, the electronics may be powered by the keypad device power supply. The electronic circuits may be designed so that the LEDs are automatically turned on after each transaction is complete for a predetermined amount of time to kill the vast majority of pathogens that could be transmitted from person to person. The LEDs may be arranged on both the left and right side of the keypad, and at the top edge of the keypad to illuminate all exposed surfaces of the keys.

DETAILED DESCRIPTION

Figure 1:
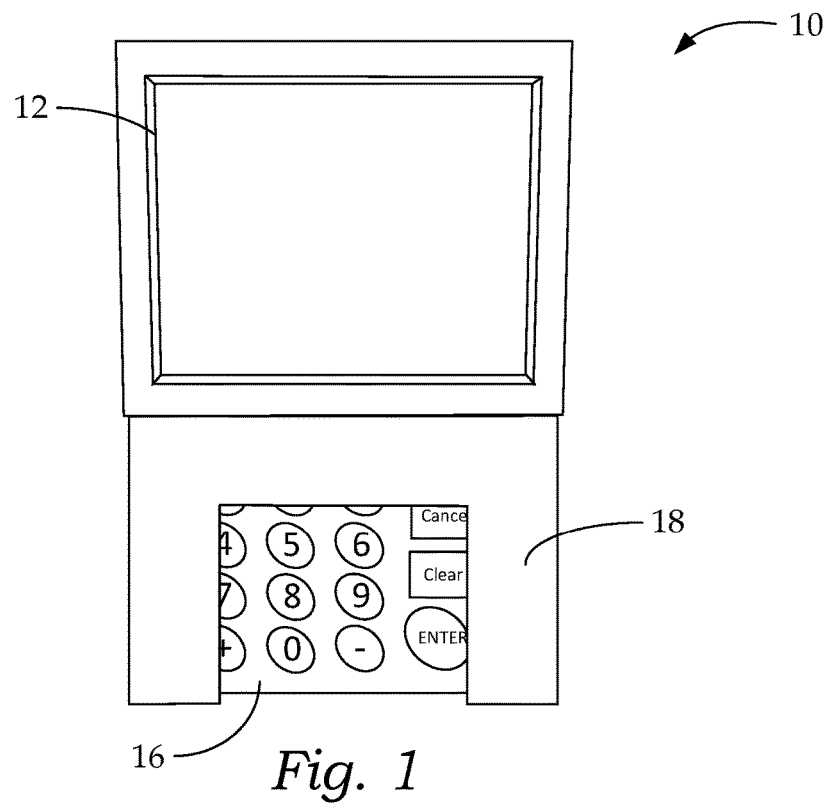
FIG. 1 is a top plan view of a keypad sterilizer of an embodiment of the present invention.
Figure 2:
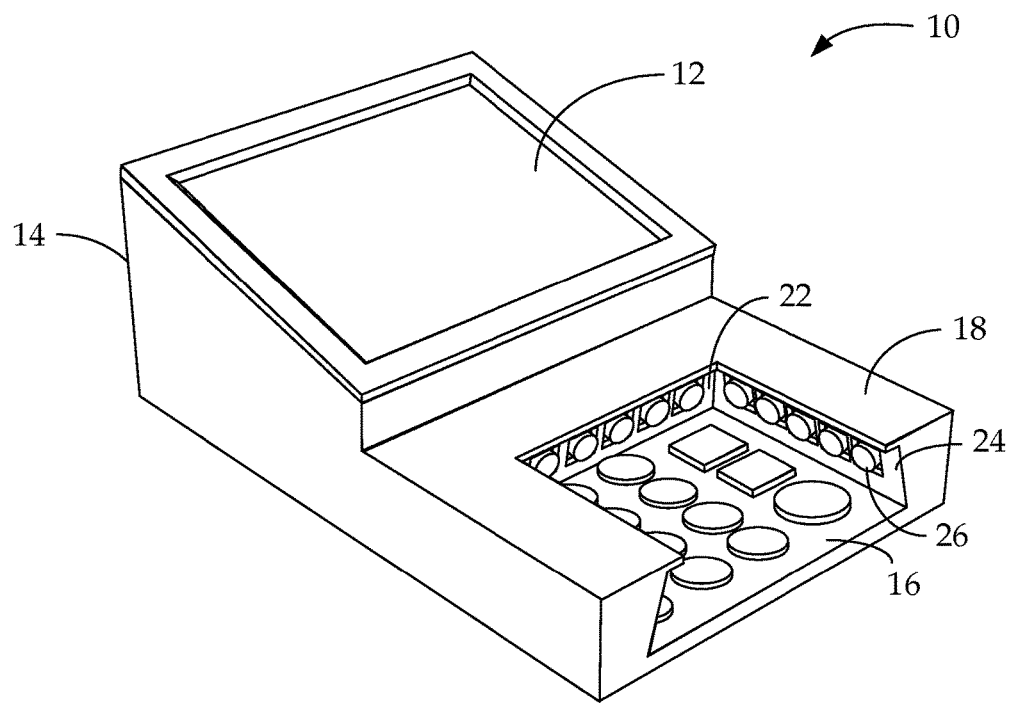
FIG. 2 is a perspective view of the keypad sterilizer of FIG. 1.

Referring initially to FIGS. 1 and 2, a point-of-sale device with an integrated keypad sterilizer of the present invention is generally indicated by reference numeral 10. The point-of-sale device 10 includes a display 12, a housing 14, a keypad 16, and a keypad shroud 18. The point-of-sale device 10 is commonly found at registers in retail stores, automatic teller machines, gasoline pumps, and other locations where payment is received using a bank or credit card. The display 12 generally provides a listing of the items purchased and instructions to the buyer, such as swipe card, enter PIN, or confirm amount, for example. The keypad shroud 18 generally provides protection for the keypad and privacy to the user when entering account information such as a PIN to complete the transaction.

The keypad shroud 18 is spaced above the keypad 16 by a left 20, back 22 and right 24 interior walls surrounding the keypad 16. The tops of the walls 20, 22 and 24 may be angled slightly inwardly toward the keypad 16. Mounted to the walls 20, 22 and 24 are one or more UV-C LEDs 26.

In a preferred embodiment, a plurality of UV-C LEDs 26 may be mounted to walls 20, 22 and 24 and directed toward keypad 16. The UV-C LEDs 26 may be configured in a surface mount package, which offers superior light output, long lifetimes, and low power consumption. The output spectrum of the UV-C LEDs 26 may be optimized for DNA-deactivation and a light output of two milliwatts or more. These UV-C LEDs 26 are ideal for applications in biofilm prevention, biofouling control and bioreactor decontamination. The UV-C LEDs 26 may have a light output viewing angle of 60 to 120 degrees, and preferably 90 to 110 degrees. The UV-C LEDs 26 may produce wavelengths of 260 nm-275 nm, for example. UV-C LED lamps have warm up times of 10 nanoseconds allowing for instant disinfection at peak powers. Due to the nature of LEDs, these devices allow for unlimited on/off cycles and an average lifetime of 10,000 hours.

Figure 3:
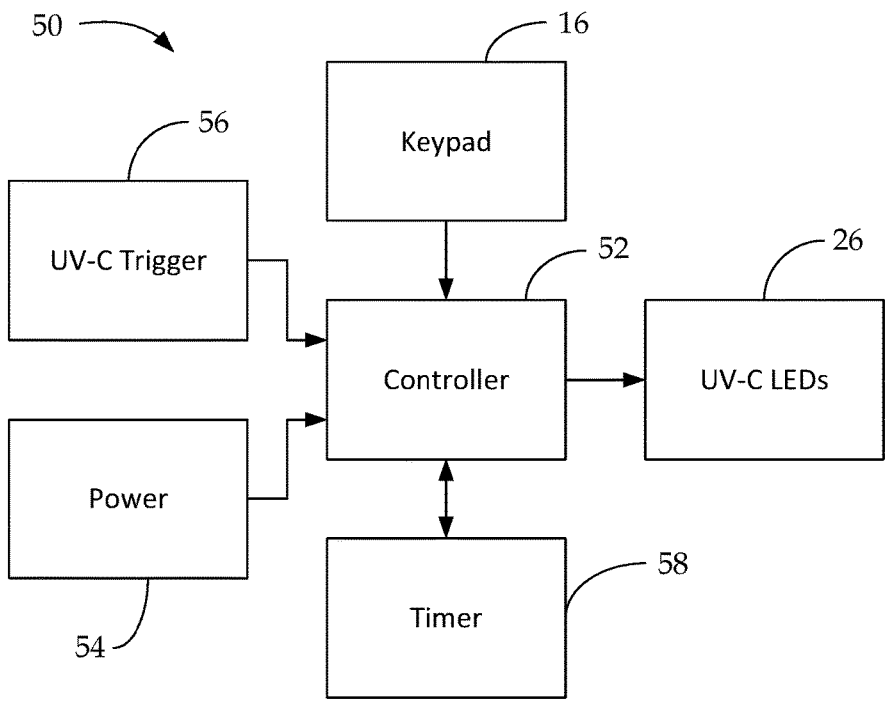
FIG. 3 is a functional block diagram of the control circuit of the keypad sterilizer of the present invention.

Referring to FIG. 3, a functional block diagram of a control circuit for the keypad sterilizer is generally indicated by reference numeral 50. The control circuit 50 includes a controller 52, which receives power 54 from the point-of-sale device 10 or other source. The controller 52 may receive input from the keypad 16, or other UV-C trigger sources 56. An internal or external timer 58 may be coupled to the controller 52 to control the energization of the UV-C LEDs 26.

In operation, the UV-C LEDs 26 may be activated in a number of ways. For example, UV-C trigger 56 may include a motion sensor incorporated in the keypad shroud 18. When the motion sensor is initially activated by detection of a person's hand in proximity of the keypad 16, the UV-C trigger 56 may send a series of motion signals to the controller 52, as long as motion is detected. The controller 52 may activate the timer 58 each time it receives a motion signal from the UV-C trigger 56. If the timer 58 expires before it receives another activation signal from the controller 52, the timer sends an activation signal to the controller 52. In response to receiving an activation signal from the timer 58 the controller 52 activates the UV-C LEDs 26 for a predetermined period of time to illuminate and sterilize the keypad 16.

By way of another example, the UV-C trigger 56 may be generated by the point-of-sales device 10. When the transaction is completed, the UV-C trigger 56 may send an activation signal to the controller 52. The controller 52 may start a countdown timer 58 and activate the UV-C LEDs 26. When the countdown timer 58 expires, a signal is sent to the controller 52, which in turn deactivates the UV-C LEDs 26. In this example, if the keypad 16 was not used, then the controller 52 may not activate the UV-C LEDs 26.

As another example, the present invention may be used in conjunction with a gasoline/diesel pump. A set of UV-C LEDs may be arranged as described above for the keypad. An additional set of UV-C LEDs may be mounted within a shroud that extends over the gas nozzle. When the gas nozzle is returned to the receptacle, the UV-C LEDs in the nozzle shroud may be activated to sterilize the gas nozzle handle. Additionally, when the transaction is complete, the UV-C LEDs coupled to the keypad may be activated to sterilize the key pad.

Figure 4:
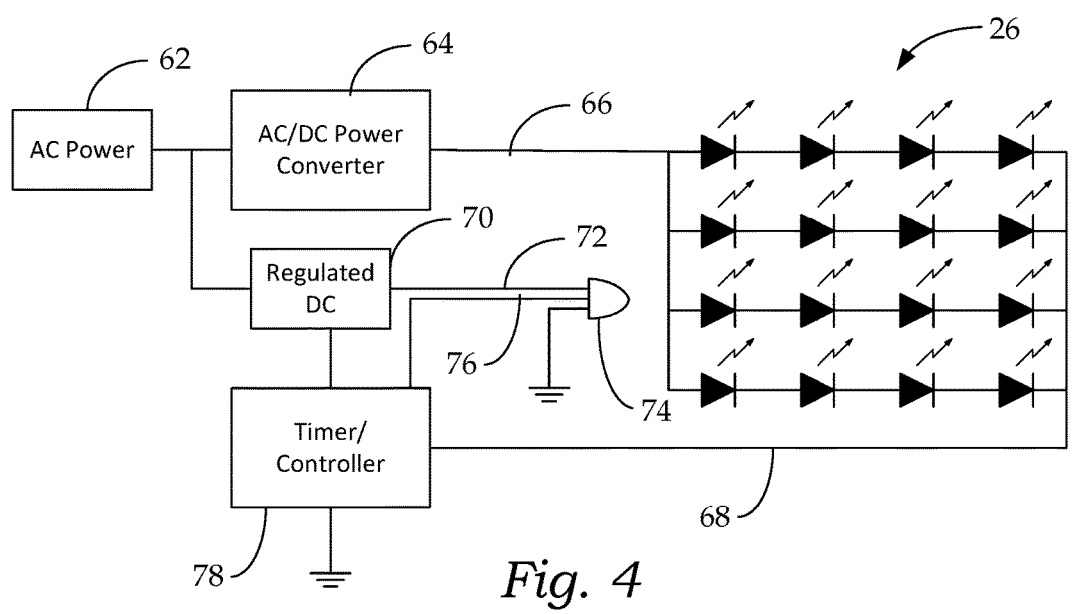
FIG. 4 is a schematic representation of the keypad sterilizer of the present invention.

Referring to FIG. 4, a schematic representation of the keypad sterilizer is generally indicated by reference numeral 60. Schematic 60 includes an AC power source 62, which provides power to an AC/DC power converter 64. The AC/DC power converter 64 converts the input AC power from a line voltage of 110/220 volts AC to a desired DC voltage such as 36 VDC on an output 66. The AC/DC power converter 64 provides power to four sets of four UV-C LED lamps 26 arranged in a series/parallel configuration with common anode coupled to the output 66, and a common cathode for each set coupled to a switched ground 68. Each series of UV-C LEDs may be mounted to a printed circuit board or other heat sink/dissipater. Further, although four sets of four UV-C LEDs are illustrated for a total of 16 UV-C LEDs, other combinations and quantities of UV-C LEDs may be used depending on the geometry of the application, surface to be sterilized, or as desired.

A regulated DC 5 volt converter 70 receives AC power from a line voltage of 110/220 volts AC, which is converted to a desired DC voltage such as 5 VDC on an output 72. The output 72 is coupled to a motion sensor 74. The output 76 of motion sensor 74 is coupled to a timer/controller 78, which is powered by converter 70. The timer/controller 78 is also coupled to switched ground 68 of the UV-C LED lamps 26.

In operation, when the motion sensor 74 detects movement, such as that of a person's hand in proximity of the keypad 16, the motion sensor 74 sends an output 76 to timer/controller 78 as long as motion is detected. When the output on line 76 goes low, a timer is initiated by the timer/controller 78. The initial timer may be set to any desired interval, such as 5 seconds. At the expiration of the initial timer, the timer/controller 78 drives common cathode output 68 to ground to activate UV-C LED lamps 26 for a second predetermined period. The second period may be varied depending on the power supplied to the UV-LED lamps 26 and the desired sterilization efficiency. If an output is received on line 76 from the motion detector 74 by the timer/controller 78 while the UV-C LEDs 26 are illuminated, the timer/controller 78 deactivates the UV-C LEDs 26, until movement is no longer detected. Then the sterilization cycle is repeated as before.

One or more additional UV-C LEDs may be arranged to illuminate other contact surfaces such as the surface of a stylist, or other instrument that may be used in combination with a keypad. Control of the additional UV-C LEDs would be as set forth above for the controller.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is as follows:

1. In combination with a point-of-sale device having a display, a housing, a keypad, a keypad shroud, and a power supply, a sterilizer comprising:
   a controller coupled to said power supply,
   an at least one UV-C LED mounted under said keypad shroud and directed to said keypad, and having an anode coupled to said power supply and a cathode coupled to said controller,
   a motion detector coupled to said power supply and said controller, and
   a timer coupled to said controller,
   wherein said controller is responsive to receiving an output from said motion detector and activating said timer when said output from said motion detector is removed,
   wherein said controller couples said cathode to ground upon expiration of said timer for a predetermined time,
   wherein said UV-C LED has an output viewing angle of 60 to 120 degrees, a light output of two milliwatts or more, and a wavelength of approximately 260 nanometers to 275 nanometers.

2. The sterilizer of claim 1, further comprising a plurality of UV-C LEDs.

3. In combination with a keypad, a sterilizer comprising:
   a power supply,
   a controller coupled to said power supply,
   an at least one UV-C LED directed at said keypad and having an anode coupled to said power supply and a cathode coupled to said controller, and directed at the keypad,
   a motion detector coupled to said power supply and said controller, and directed at the keypad, and
   a timer coupled to said controller,
   wherein said controller is responsive to receiving an output from said motion detector and activating said timer when said output from said motion detector is removed,
   wherein said controller couples said cathode to ground upon expiration of said timer for a predetermined time, wherein said UV-C LED has an output viewing angle of 60 to 120 degrees, a light output of two milliwatts or more, and a wavelength of approximately 260 nanometers to 275 nanometers.

4. The sterilizer of claim 3, further comprising a plurality of UV-C LEDs directed at the keypad.

5. In combination with a keypad, a sterilizer comprising:
a power supply,
a controller coupled to said power supply,
an at least one UV-C LED directed at said keypad and having an anode coupled to said power supply and a cathode coupled to said controller, and directed at the keypad,
a motion detector coupled to said power supply and said controller, and directed at the keypad, and
a timer coupled to said controller,
wherein said controller is responsive to receiving an output from said motion detector and activating said timer when said output from said motion detector is removed,
wherein said controller couples said cathode to ground upon expiration of said timer for a first predetermined time of at least 10 seconds,
wherein said controller decouples said cathode from ground at the expiration of said first predetermined time,
wherein said controller decouples said cathode from ground if said controller receives said output from said motion detector during said first predetermined time,
wherein said UV-C LED has an output viewing angle of 60 to 120 degrees, a light output of two milliwatts or more, and a wavelength of approximately 260 nanometers to 275 nanometers.

6. The sterilizer of claim 5, further comprising a plurality of UV-C LEDs directed at the keypad.

* * * * *